(12) United States Patent
Engels

(10) Patent No.: US 7,440,106 B2
(45) Date of Patent: Oct. 21, 2008

(54) APPARATUS ON A SPINNING PREPARATION FOR DETECTING FOREIGN OBJECTS OF PLASTIC MATERIAL

(75) Inventor: Guido Engels, Rommerskirchen (DE)

(73) Assignee: Trutzschler GmbH & Co., KG., Monchengladbach (DE)

( * ) Notice: Subject to any disclaimer, the term of this patent is extended or adjusted under 35 U.S.C. 154(b) by 347 days.

(21) Appl. No.: 10/952,930

(22) Filed: Sep. 30, 2004

(65) Prior Publication Data

US 2005/0078306 A1 Apr. 14, 2005

(30) Foreign Application Priority Data

Oct. 10, 2003 (DE) ................. 103 47 240

(51) Int. Cl.
*G01N 21/84* (2006.01)

(52) U.S. Cl. ..................................... 356/429

(58) Field of Classification Search ......... 356/429–430, 356/364–370
See application file for complete search history.

(56) References Cited

U.S. PATENT DOCUMENTS

| | | | | |
|---|---|---|---|---|
| 2,824,488 | A | * | 2/1958 | Bridges et al. ............... 356/73 |
| 3,602,597 | A | * | 8/1971 | Sproul ........................ 356/368 |
| 3,990,087 | A | * | 11/1976 | Marks et al. ................ 396/331 |
| 4,410,277 | A | * | 10/1983 | Yamamoto et al. .......... 356/366 |
| 4,839,943 | A | * | 6/1989 | Leifeld ........................ 19/80 R |
| 5,125,514 | A | | 6/1992 | Oehler et al. |
| 5,270,787 | A | | 12/1993 | Shofner et al. |
| 5,315,367 | A | | 5/1994 | Salvador et al. |
| 5,598,266 | A | | 1/1997 | Cornuejols |
| 6,535,284 | B1 | * | 3/2003 | Hajduk et al. ............... 356/367 |

FOREIGN PATENT DOCUMENTS

| | | |
|---|---|---|
| DE | 36 44 535 A1 | 7/1988 |
| DE | 36 44535 A1 | 7/1988 |
| DE | 296 23 620 U1 | 2/1999 |
| DE | 693 24 557 T2 | 9/1999 |
| DE | 199 41 723 A1 | 3/2001 |
| EP | 0 364 786 B1 | 4/1990 |
| EP | 0 604 875 A2 | 7/1994 |
| EP | 1 123 995 A1 | 8/2001 |
| JP | 9-269296 A | 10/1997 |

* cited by examiner

*Primary Examiner*—Tarifur R. Chowdhury
*Assistant Examiner*—Isiaka O Akanbi
(74) *Attorney, Agent, or Firm*—Venable LLP; Robert Kinberg

(57) ABSTRACT

A detection apparatus in spinning preparation for detecting foreign objects of plastics material in or amongst fiber material. The apparatus includes a source of polarised light and a transport arrangement for transporting the fiber material such that the fiber material is irradiated by the polarized light source. An analyzer is arranged to render visible any change in a plane of polarization caused by the irradiation of the foreign objects of plastics material in or amongst the fiber material and a detector device is arranged to capture an image of contrast differences and/or color shifts in the fiber material rendered visible by the analyzer. The detection apparatus further includes an evaluating unit arranged to process the image to identify the foreign objects for removal.

30 Claims, 6 Drawing Sheets

APPARATUS ON A SPINNING PREPARATION FOR DETECTING FOREIGN OBJECTS OF PLASTIC MATERIAL

CROSS REFERENCE TO RELATED APPLICATION

This application claims priority from German Application No. 103 47 240.1 filed Oct. 10, 2003, the entire disclosure of which is incorporated herein by reference

BACKGROUND OF THE INVENTION

The invention relates to an apparatus for use in spinning preparation for detecting foreign objects of plastics material, such as polypropylene bands, fabric and films and the like, in or among fibre material, especially fibre flocks, for example, of cotton. The fibre material may in particular, but not exclusively, be fibre flocks being removed (opened) from bales of textile fibre, during which process a foreign object detector and the fibre flocks are movable relative to one another, the foreign object detector comprising a transmitter and a receiver for electromagnetic waves or rays and an evaluating device for distinguishing the foreign objects from the fibre flocks.

In a known apparatus (DE 36 44 535 A1), the fibre flocks are arranged in a loose pile on a moving conveyor belt. A transmitter for the electromagnetic waves or rays is arranged above the conveyor belt with the pile of fibre flocks. A receiver is located between the upper and lower belt regions. The material of the conveyor belt is a material that is permeable to electromagnetic waves or rays. The loose pile of flocks is then irradiated. The foreign objects are often polypropylene bands. The apparatus enables the form (shape) colour, size or brightness of foreign objects to be determined. The recognised outwardly differing features of the foreign objects are used to differentiate them, by a comparison process, from the good fibres of the fibre flocks.

It is an aim of the invention further to improve the apparatus for detecting foreign objects of plastics materials, such as polypropylene bands, fabric and films, and the like.

SUMMARY OF THE INVENTION

The invention provides a detection apparatus for detecting foreign objects of plastics material in or amongst fibre material, comprising
 a source of polarised light;
 a transport arrangement for so transporting the fibre material that it is irradiated by the source; and
 a detector device arranged to receive light from the fibre material.

The measures according to the invention enable a reliable detection of light-coloured or transparent plastics foreign objects that are responsive to polarised light to be achieved. It is advantageous therein that in particular those foreign objects having only a slight optical contrast with the good fibres (textile fibres) can be detected. The plastics materials occur in many cases in the form of packaging films or packaging fabrics. According to the invention, not only relatively large parts but also foreign fibres are recognised and detected.

The foreign objects of plastics material may be able to rotate the polarisation vector of the polarised light. The light may be linearly polarised, circularly polarised, or elliptically polarised. The light source and the detector device may be arranged on different sides of the fibre flocks (transmitted light arrangement). The light source and the detector device may be arranged on the same side of the fibre flocks (incident light arrangement). Depolarisation may be effected for detection. Reflection-suppression may be effected for detection. Foreign objects of plastics material may change the polarised light by anisotropies (such as double refraction) such that the light is rendered visible by the analyser of the detector device. The fibre material may be arranged in a channel of glass or the like. The fibre material may be conveyed through a channel pneumatically. The fibre material may be arranged on a conveyor belt. The fibre material may be arranged with a roller, e.g. detaching roller.

The roller may rotate rapidly. There may be provided a background that is diffuse; reflecting, for example, mirror-like; or luminous. The detector device may be a line-scan camera. The detector device may be a matrix camera. The detector device may comprise light sensors. Detection may take place in colour. Detection may take place in black and white. A polariser may be arranged between light source and fibre material. A light source that emits polarised light may be present. A polariser may be integrated on or within the light source. An analyser may be arranged between the fibre material and the detector device. A detector that also acts as analyser may be present. The analyser may be integrated on or within the detector. Light-refracting elements, for example prisms, may be arranged in the ray path. In addition or instead, lenses may be arranged in the ray path.

A device for removing foreign objects may be arranged downstream of the evaluating device. The evaluating device and the removal device may be electrically connected with one another by a control or switching device. The device may be arranged downstream of a bale opener. The device may be arranged in or downstream of a cleaning device. The device may be arranged in or downstream of a carding machine. The device may be arranged in or downstream of a foreign fibre separator. The device may be arranged in or downstream of a foreign object separator.

Anisotropies such as the double refractive effect of the foreign objects may be used for detection. Selectively absorbing behaviour (dichroism) of the foreign objects may be used for detection. Optically active behaviour (rotary dispersion) of the foreign objects may be used for detection. The detector device is advantageously able to distinguish sheet-form from fibre-form foreign objects on the basis of its resolution.

The invention also provides an apparatus in spinning preparation for detecting foreign objects of plastics material, such as polypropylene bands, fabric and films and the like, in or among fibre flocks, for example, of cotton, that are being removed (opened) from bales of textile fibre, during which process a foreign object detector and the fibre flocks are movable relative to one another, the foreign object detector comprising a transmitter and a receiver for electromagnetic waves or rays and an evaluating device for distinguishing the foreign objects from the fibre flocks, characterised in that a source of polarised light that cooperates with at least one detector device (camera) acts on the fibre material (fibre flocks, fibre flock web), the fibre material being irradiated, with light passing through light-coloured and/or transparent sheet-form foreign objects of plastics material, and the detector device being capable of distinguishing sheet-form foreign objects from fibrous plastics items (synthetic fibres).

DETAILED DESCRIPTION OF PREFERRED EMBODIMENTS

Figure 1:
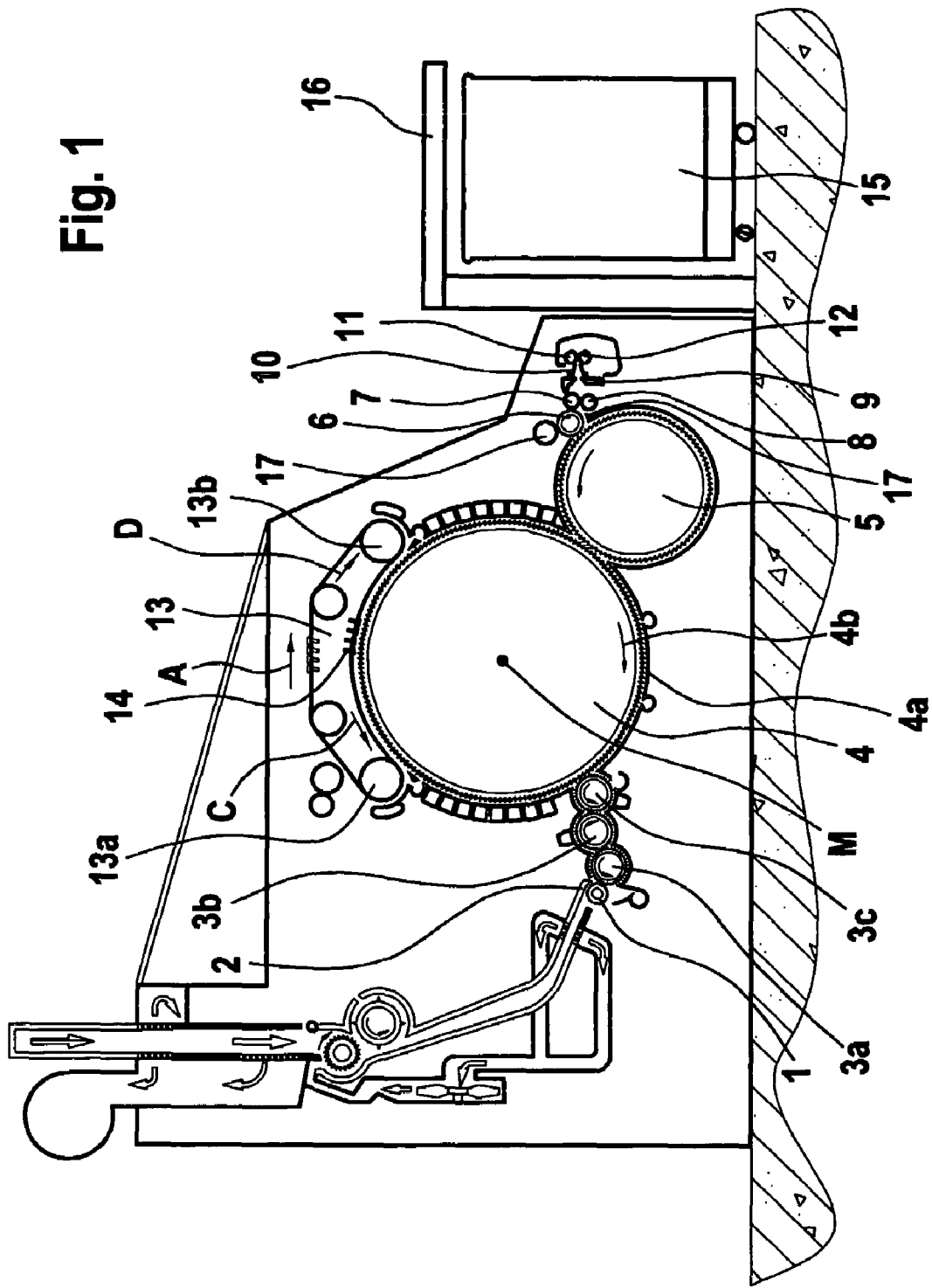
FIG. 1 is a schematic side view of a carding machine with a first embodiment of apparatus according to the invention.

FIG. 1 shows a carding machine, for example, a TC 03 Card made by Trützschler GmbH & Co. KG of Mönchengladbach, Germany, with feed roller 1, feed table 2, licker-ins 3a, 3b, 3c, cylinder 4, doffer 5, stripping roller 6, squeezing rollers 7, 8, web-guide element 9, web funnel 10, take-off rollers 11, 12, revolving card top 13 with guide rollers 13a, 13b and card flat bars 14, can 15 and can coiler 16. The directions of rotation of the rollers are shown by curved arrows. The letter M denotes the midpoint (axis) of the cylinder 4. 4a denotes the clothing and 4b the direction of rotation of the cylinder 4. The letter C denotes the direction of rotation of the revolving card top 13 in the carding position and the letter D denotes the return transport direction of the card flat bars 14. Beneath the stripping roller 6 there is arranged a stationary supporting and guiding member 17; the upper squeezing roller 7 is arranged in close proximity to the stripping roller 6. The directions of rotation of the cylinder 4 and the rollers are represented by respective curved arrows. The supporting and guiding member 17 serves to receive the apparatus 18 according to the invention. The letter A denotes the working direction.

Figure 2:
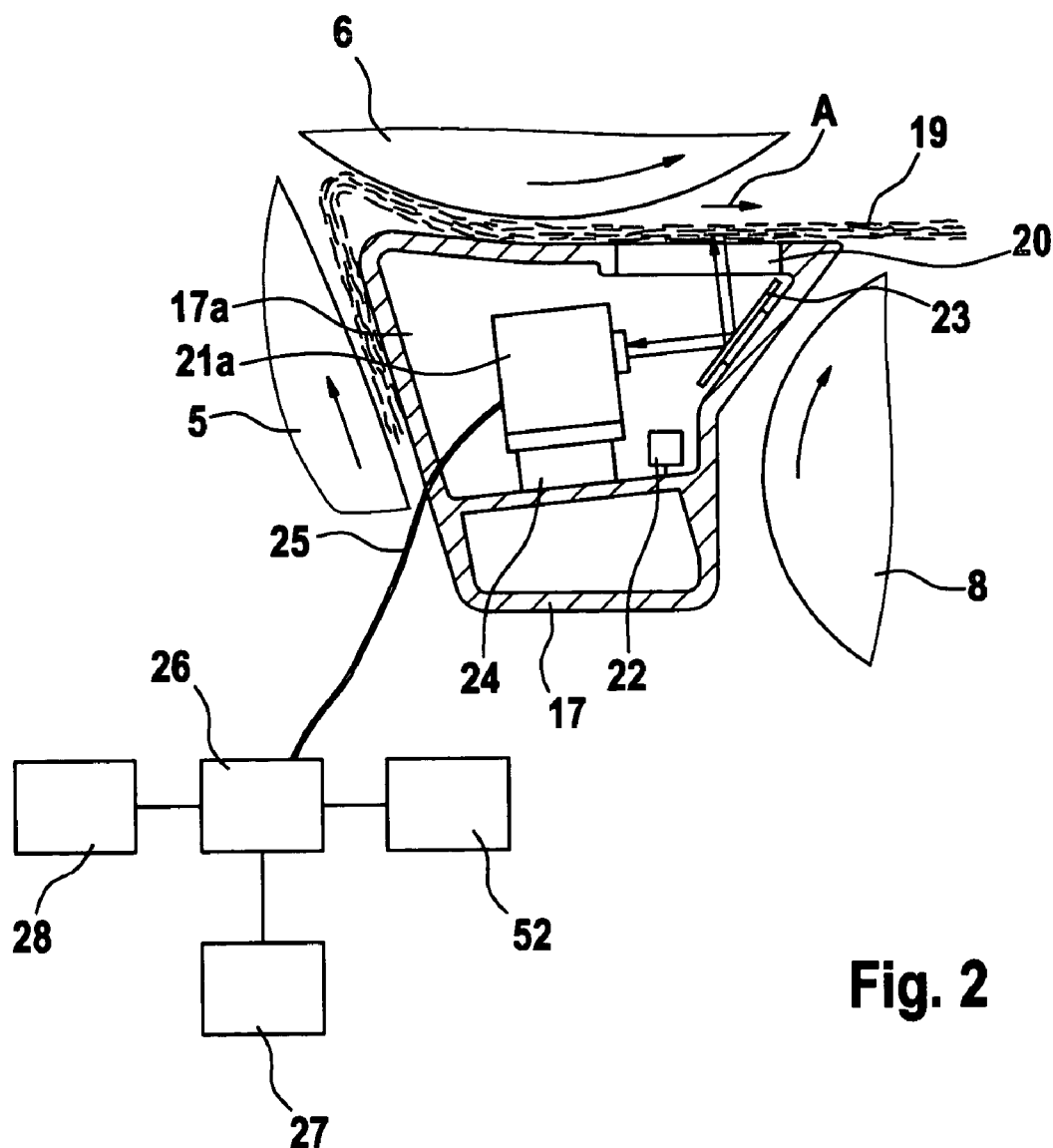
FIG. 2 shows the first embodiment on the carding machine according to FIG. 1 with the fibre web to be examined.

In FIG. 2, the reference number 21 denotes the region in which the removed fibre web 19 passes from the stripping roller 6 to the squeezing rollers 7, 8. The supporting and guiding member 17 has essentially a four-cornered cross-section. The upper surface is slightly concavely curved. The radius of curvature of the curve of the upper surface is greater than the radius of curvature of the stripping roller 6. The arrow A indicates the running direction of the fibre web 19. The element 17 is in the form of a housing, a transparent window 20 being provided in the sliding contact region. The fibre web 19 is located initially on the clothing of the doffer 5, is guided in the roller nip between doffer 5 and stripping roller 6 around and over the clothing 6a of the stripping roller 6, is detached from the stripping roller 6 a little way after the region of the perpendicular diameter, is guided in the region of the window 20 in direction A, following the end region runs completely freely and finally enters the roller nip between the squeezing rollers 7, 8 and passes between these. The upper surface of the element 17 faces towards the clothing 6a of the stripping roller 6. With its one end region, the element 17 is associated with the roller nip between doffer 5 and stripping roller 6. The other end region is arranged in the region between stripping roller 6 and squeezing rollers 7, 8, the edge thereof being aligned in the direction towards the roller nip between the squeezing rollers 7, 8. The element 17 is an extruded profile, for example, of aluminium, with an inner cavity 17a. Fixed cameras $21a$ to $21_1$, for example, diode matrix cameras, an illuminating device 22 arranged to generate polarised light, (for example, comprising several light-emitting diodes), and a reflecting mirror 23 are arranged in the inner cavity 17a of the housing 17. The reflecting mirror 23 is arranged at an angle between the objective of the cameras $21a$ to $21_1$ and the illuminating device 22 on the one hand and the inside of the window 20 on the other hand. The fibre web 19 runs over the outside of the window 20 in direction A. The window 20, for example of glass, is kept clean by contact with the moving fibre material. The cameras $21a$ to $21_1$ (only camera $21a$ is shown in FIG. 2) are arranged on a common support 24, which is secured to the element 17. The reference numeral 25 denotes an electrical lead. The reference numeral 26 denotes an electronic evaluating unit to which the display device 27 and/or a separating device 28 (see FIGS. 4 and 5) are connected. The reference numeral 52 denotes the machine control for the card (see FIG. 1).

Figure 3:
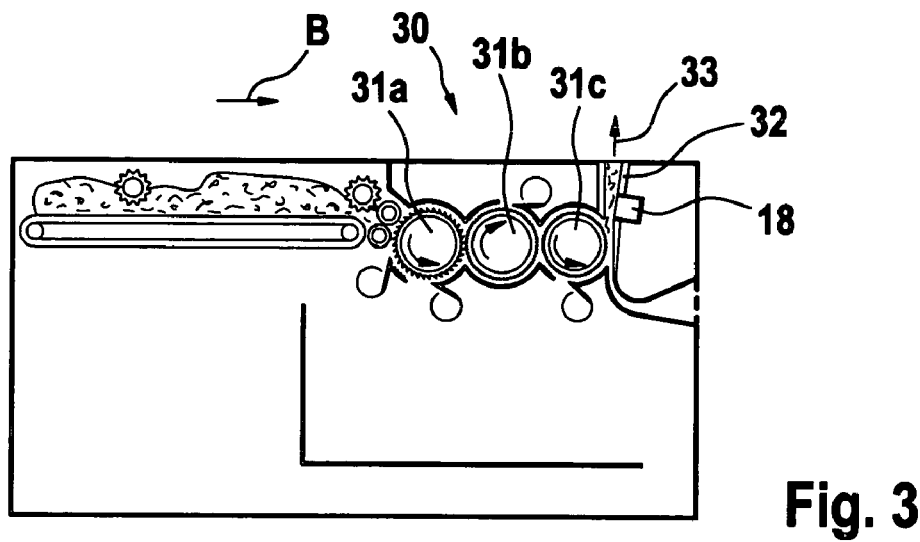
FIG. 3 is a schematic side view of a second embodiment of apparatus according to the invention on a cleaner, associated with the removed fibre material.

In the arrangement of FIG. 3, an apparatus 18 according to the invention is mounted on a cleaning machine 30, e.g. a CLEANOMAT VCT 3 cleaning machine made by Trützschler GmbH & Co. KG. The apparatus 18 is associated with the fibre tuft material 33, e.g. cotton, removed by the last roller 31c—viewed in the working direction B—of the multiple roller cleaner 30 and discharged through a pipeline 32. The apparatus 18 is connected to the machine control system and allows unwanted polypropylene foreign objects in the cotton fibre material to be detected.

Figure 4:
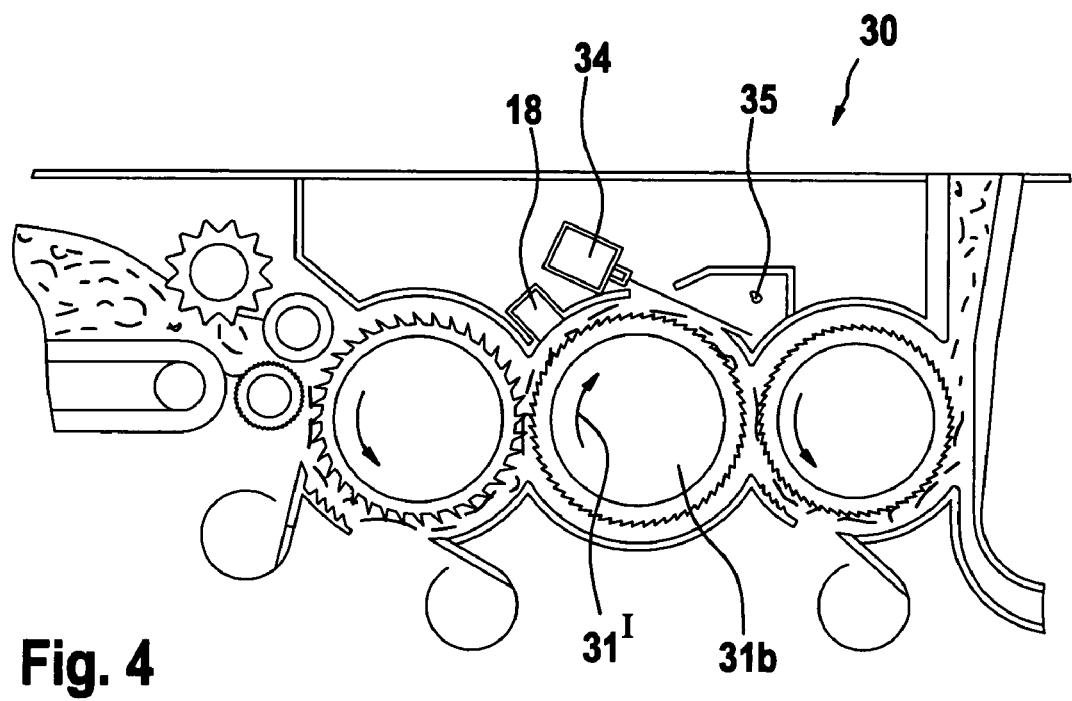
FIG. 4 is a schematic side view of a further embodiment of the invention associated with a high-speed roller of a cleaner with a pneumatic foreign object separation device.

Referring to FIG. 4, an apparatus 18 according to the invention and a pneumatic foreign object separation device 34 are associated with the middle roller 31b of the cleaner 30, viewed in the direction of rotation 31' of the roller 31b.

Figure 5:
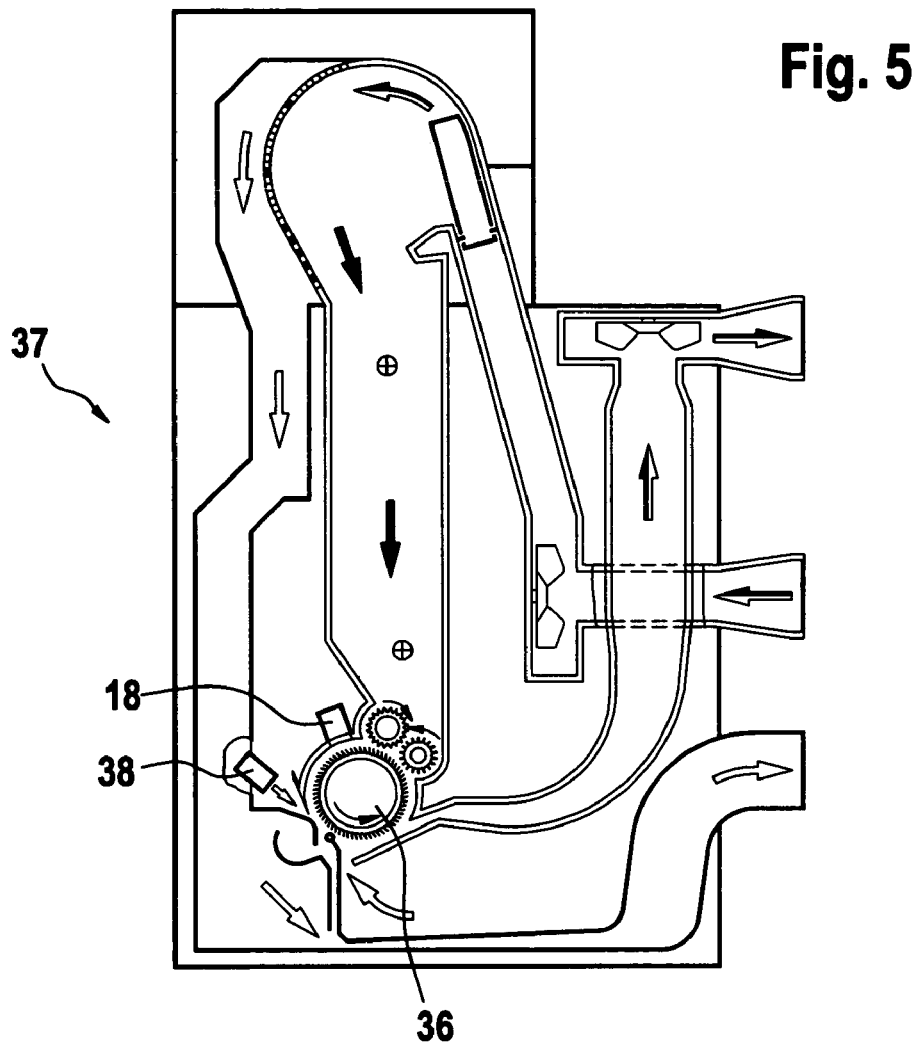
FIG. 5 is a schematic side view of a further embodiment on a foreign object recognition and separation device with a high-speed roller.

In the arrangement of FIG. 5, the apparatus 18 according to the invention is associated with the high-speed roller 36 of a foreign object recognition and separation device 37, e.g. a SECUROMAT SCFO device made by Trützschler GmbH & Co. KG. Viewed in the direction of rotation of the roller 36, downstream of the device 37 there is arranged a pneumatic foreign object separating device 34, which comprises a plurality of blast nozzles 38 across the width of the machine 37. The machine control system (52, see FIG. 2.) to which the apparatus 18 according to the invention and the device 34 are connected, always functions in response only to one nozzle 38a to 38n or to two adjacent nozzles 38a to 38n, in the operative region of which the foreign object 35 has been detected. As a consequence, only a few fibre tufts (only 1-2 g) of cotton per separation process are removed. This permits a selective, sensitive adjustment of the system to enable even small portions to be separated out without allowing an unduly high loss of fibre material. The foreign objects 35 and the fibre material are located on the roller 36, which has a saw-tooth or needle clothing.

Figure 6:
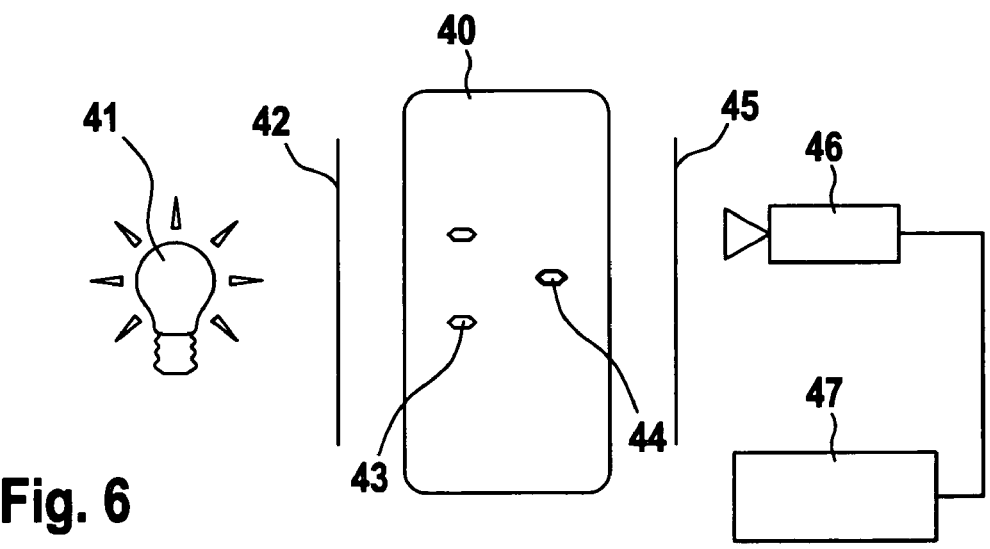
FIG. 6 is a front view of an embodiment of the invention associated with a transport channel and having a transmitted light arrangement.

FIG. 6 shows an arrangement in which an apparatus of the invention is associated with a glass channel 40, the apparatus being operable as a transmitted light arrangement: the light radiating from a light source 41 is converted by means of a polariser 42 into linearly, circularly or even elliptically polarised light. This shines through the material to be inspected that is being transported through the transparent channel 40 through the optical arrangement. Whereas with cotton 43 and other natural constituents of the cotton 43 there is no change in the light, the plastics foreign object 44 produces a change in the plane of polarisation of the light. This change can be rendered visible by means of the analyser 45. Contrast differences and colour shifts occur relative to the other good material. These are picked up by one or more detectors 46 (a camera in FIG. 6) and processed by an associated evaluating unit 47, so that an automatic separation (not shown) of the detected plastics items 44 can be carried out.

Figure 7:
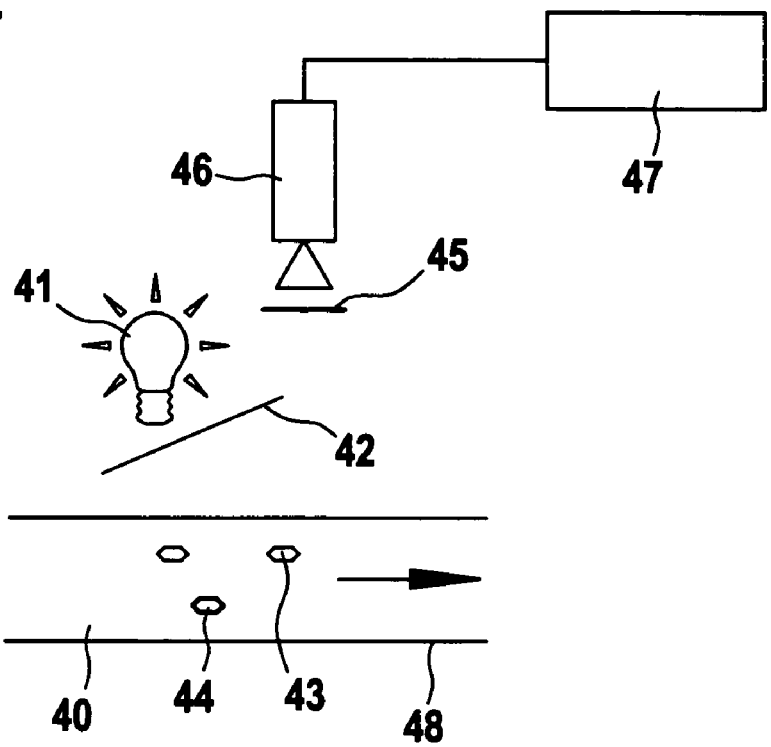
FIG. 7 is a side view of an embodiment of the invention associated with a transport channel and having an incident light arrangement.

FIG. 7 shows an arrangement which is the same, in principle, as FIG. 6, except that an incident light arrangement is used. The essential difference is that both illuminating means 41 and detector 46 (a camera in FIG. 7) are situated on the same side of the material. The material is also separated here from the measuring arrangement by a window. The background 48 can be provided both by conveyor belts or rollers, which simultaneously serve to transport the material, and by fixed surfaces with lamps or surfaces with diffuse and shiny to mirror-like reflecting properties. Depending on the background used, the evaluation has to be effected differently, the important factor being that there is always an assessable change in light intensity or colour between cotton material 43 and the plastics items 44. Depending on the evaluating method used, a contrast between background 48 and the material can be present/desirable or not.

Figure 8:
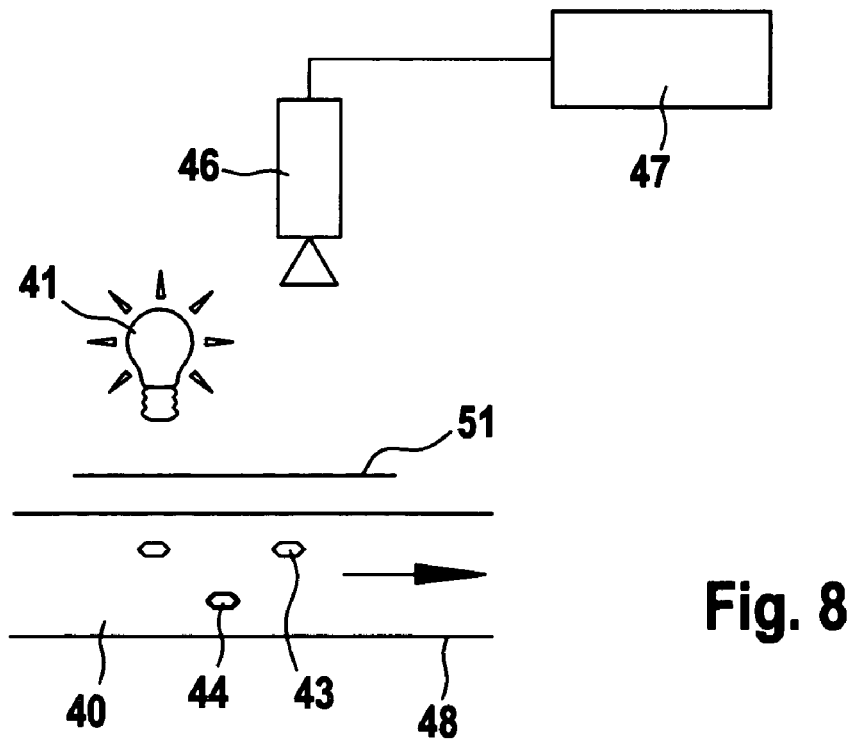
FIG. 8 is a side view of a variant of the apparatus of FIG. 7 in which the polariser and the analyser are combined in one component.

A further modification of the arrangement of FIG. 7 is illustrated in FIG. 8. Here, the elements polariser 42 and analyser 45 are combined in one component 51. Here too, surfaces of diffuse or shiny to reflective construction come into consideration as the background.

Figure 9:
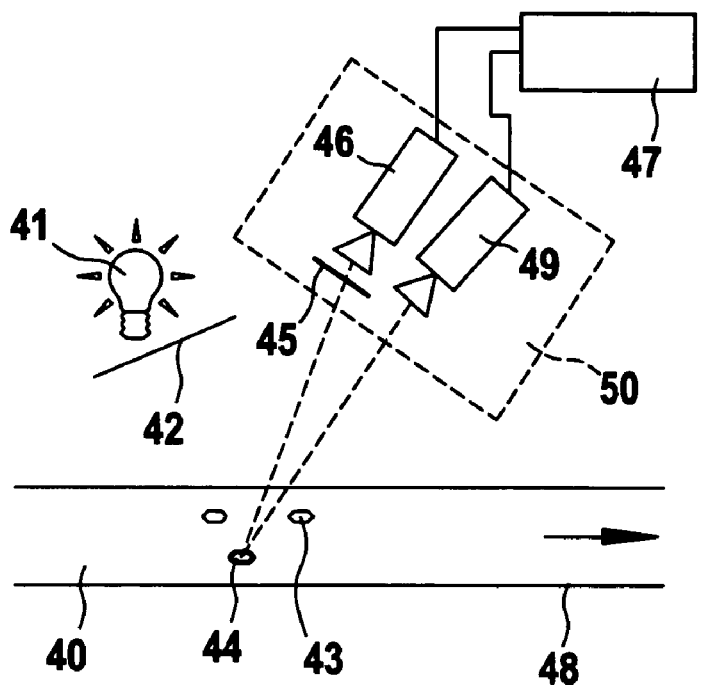
FIG. 9 shows a further variant of the embodiment of FIG. 7 with two cameras.

Yet other embodiments comprise working with one or more pairs of cameras/detectors, the cameras of the or each pair being directed directly onto the same spot in the flow of material, as illustrated in FIG. 9. One camera 46 is equipped with an analyser 45, which is arranged so that the analyser 45 suppresses reflection. The other camera 49 of the pair does not need this analyser 45 and is spatially arranged so that a maximum light reflection occurs with plastics films. Both cameras 46 and 49 are aligned with respect to one another so that they both take exactly the same image section. Even if the cameras are not aligned, however, this can be created by a calibration in the evaluating unit. In the evaluation, both images of the spatially identical scene (one with and one without light reflection) are now assessed by comparison after a previously possible signal conditioning. One option for this would be, for example, to compute the two image signals to a third image, for example, by means of a difference or quotient process.

The advantage of using two cameras is that the slight differences between image with light reflection and image without light reflection can easily be brought out, so that reliable detection is possible.

In order to simplify the mechanical construction, it is also possible to house both cameras/detectors in a common housing 50, optionally with a common objective, the interior construction of which is designed in such a way, for example, by using beam splitters, prisms etc. or by the exact alignment of the two sensors relative to one another, that both image signals are received exactly from the same point or a spatial calculation or calibration in the evaluating unit 47 is easily possible.

Figure 10:
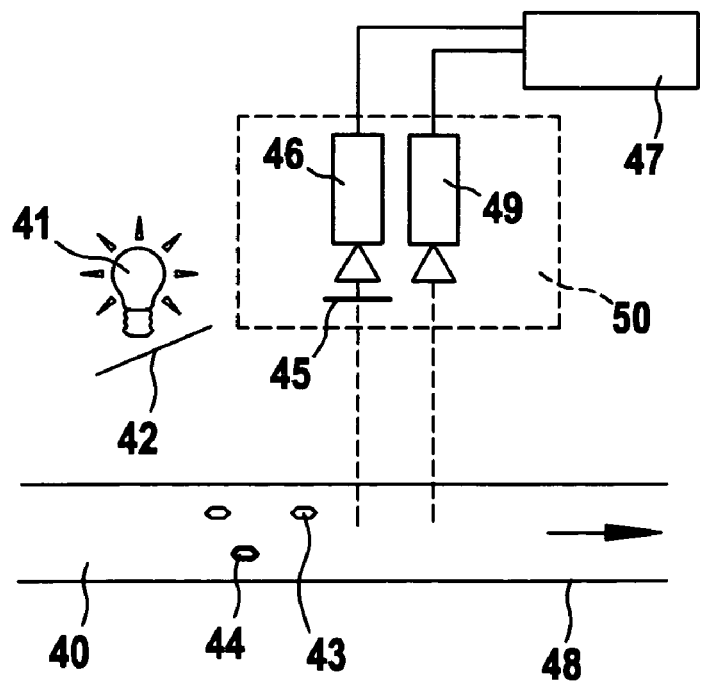
FIG. 10 shows a further embodiment with two cameras.

If the material is being conveyed by a conveyor belt or a needle roller, in which case the spatial arrangement of the individual fibres or fibre bundles relative to one another does not change, that is, the transport is merely linear, then both cameras 46 and 49, as shown in FIG. 10, can scan the surface also at different points. The evaluation is then effected in the manner described for FIG. 9.

The described arrangements shown in FIGS. 6 to 10 can basically be used with linearly or circularly polarised light. In instances of the arrangements shown in FIGS. 6 to 8 it is advantageous, however, to use circularly polarised light, because this enables independence from the effect of the rotated position of the plastics items 44 to be achieved.

Although the foregoing invention has been described in detail by way of illustration and example for purposes of understanding, it will be obvious that changes and modifications may be practised within the scope of the appended claims.

What is claimed is:

1. A detection apparatus for detecting foreign objects of plastics material in or amongst flocks of fibre material, comprising:
   a source of polarised light;
   a transport arrangement for transporting the flocks of fibre material such that each flock of fibre material is irradiated by the source of polarised light;
   an analyzer arranged to suppress reflection of the polarised light from the flocks of fibre material and render visible any change in a plane of polarization caused by the irradiation of the foreign objects of plastics material in or amongst the flocks of fibre material;
   a detector device arranged to capture an image of contrast differences and/or color shifts rendered visible by the analyzer; and
   an evaluating unit arranged to process the image to identify the foreign objects for removal.

2. An apparatus according to claim 1, in which the detector device is arranged to detect foreign objects of plastics material that rotate the polarisation vector of the polarised light.

3. An apparatus according to claim 1, in which the source of polarised light is arranged to emit linearly polarised light.

4. An apparatus according to claim 1, in which the source of polarised light is arranged to emit circularly polarised light.

5. An apparatus according to claim 1, in which the source of polarised light is arranged to emit elliptically polarised light.

6. An apparatus according to claim 1, in which the source of polarised light and the detector device are arranged on different sides of the fibre material.

7. An apparatus according to claim 1, in which the light source and the detector device are arranged on the same side of the fibre material.

8. An apparatus according to claim 1, wherein depolarization of the light associated with the foreign objects is used for detection.

9. An apparatus according to claim 1, in which the transport arrangement comprises a channel of a transparent material within which the fibre material is located.

10. An apparatus according to claim 1, in which the transport arrangement comprises a conveyor belt upon which the fibre material is arranged.

11. An apparatus according to claim 1, in which the transport arrangement comprises a roller.

12. An apparatus according to claim 1, in which the detector device is arranged to view the fibre material against a viewing background selected from diffuse backgrounds; reflecting backgrounds; and luminous backgrounds.

13. An apparatus according to claim 1, in which the detector device is a camera.

14. An apparatus according to claim 1, in which the source of polarised light comprises a light source and a polariser arranged between the light source and the fibre material.

15. An apparatus according to claim 1, in which the source of polarised light comprises a light source that emits polarised light.

16. An apparatus according to claim 1, in which the source of polarised light comprises a light source and a polariser integrated on or within the light source.

17. An apparatus according to claim 1, in which the analyser is arranged between the fibre material and the detector device.

18. An apparatus according to claim 1, which comprises the analyser integrated on or within the detector device.

19. An apparatus according to claim 1, in which light-reflecting elements and/or light-refracting elements are arranged in the ray path.

20. An apparatus according to claim 1, in which anisotropies associated with the foreign objects can be used for detection.

21. An apparatus according to claim 1, in which a double refractive effect of the foreign objects can be used to assist detection.

22. An apparatus according to claim 1, in which selectively absorbing behaviour of the foreign objects can be used for detection.

23. An apparatus according to claim 1, in which optically active behaviour of the foreign objects can be used for detection.

24. An apparatus according to claim 1, in which the detector device is able to distinguish sheet-form from fibre-form foreign objects on the basis of a resolution of the respective foreign object.

25. An apparatus according to claim 1, further comprising, downstream of the detector device, a removal device for removing the detected foreign objects.

26. An apparatus according to claim 25, in which the detector device and the removal device are electrically connected with one another by a control or switching device.

27. An apparatus according to claim 1, which is arranged in a location selected from: downstream of a bale opener; in or downstream of a cleaning device; in or downstream of a carding machine; in or downstream of a foreign fibre separator; and in or downstream of a foreign object separator.

28. An apparatus according to claim 22, wherein the selectively absorbing behaviour comprises dichroism.

29. An apparatus according to claim 23, wherein the optically active behaviour comprises rotary dispersion.

30. A foreign object recognition and separation device comprising:
   a pneumatic foreign object separating device; and
   a detection apparatus disposed upstream of the pneumatic foreign object separating device and configured to detect foreign objects of plastics material in or amongst flocks of fibre web material, the detection apparatus including:
   a source of polarised light;
   a transport arrangement for transporting the flocks of fibre web material such that each flock of the fibre web material is irradiated by the source of polarised light;
   an analyzer arranged to suppress reflection of the polarised light from the flocks of fibre material and render visible any change in a plane of polarization caused by the irradiation of the foreign objects of plastics material in or amongst the flocks of fibre material;
   a detector device arranged to capture an image of contrast differences and/or color shifts rendered visible by the analyzer; and
   an evaluating unit arranged to process the image to identify the foreign objects for removal, wherein the pneumatic foreign object separating device operates to remove the foreign objects from the flocks of fibre web material when the detection apparatus detects the foreign objects.

* * * * *